United States Patent [19]

Evert

[11] Patent Number: 5,445,610

[45] Date of Patent: Aug. 29, 1995

[54] PORTABLE PERITONEAL DIALYSIS CYCLER

[75] Inventor: Carl F. Evert, Cincinnati, Ohio

[73] Assignee: University of Cincinnati, Cincinnati, Ohio

[21] Appl. No.: 5,904

[22] Filed: Jan. 15, 1993

[51] Int. Cl.[6] .............................................. A61M 1/00
[52] U.S. Cl. .................................................... 604/29
[58] Field of Search ........................... 604/65, 80–81, 604/246, 4–6, 27–29, 33–34, 249–250, 83, 174, 283, 410

[56] References Cited

U.S. PATENT DOCUMENTS

| | | |
|---|---|---|
| 4,270,048 | 5/1981 | Liebing . |
| 4,412,917 | 11/1983 | Ahjopalo . |
| 4,413,988 | 11/1983 | Handt et al. . |
| 4,560,472 | 12/1985 | Granzow et al. . |
| 4,585,436 | 4/1986 | Davis et al. . |
| 4,586,920 | 5/1986 | Peabody . |
| 4,718,890 | 1/1988 | Peabody . |
| 4,747,822 | 5/1988 | Peabody . |
| 4,994,026 | 2/1991 | Fecondini . |
| 5,004,459 | 4/1991 | Peabody et al. . |

OTHER PUBLICATIONS

The Portable Inpersol Cycler TM 1000, Abbott Laboratories, Jan., 1989.
Amicon Equaline TM Fluid Control System, Amicon Division, W. R. Grace & Co.1, Publication No. 1 261, 1988.

*Primary Examiner*—C. Fred Rosenbaum
*Assistant Examiner*—Manuel Mendez
*Attorney, Agent, or Firm*—Frost & Jacobs

[57] ABSTRACT

A portable, gravity-type peritoneal dialysis cycler for controlling during each dialysis cycle the volumetric flows of an exchange fluid into and out of the peritoneal space of a patient, and the dwell time of the exchange fluid therein. The cycler comprises an easily assembled vertical stand supporting a load cell from which a pair of exchange fluid filled bags are suspended above the level of the patient's peritoneal space and a pair of drain bags are suspended therebelow. The single load cell is connected to an electronic scale circuit. A single tube is connected at one end to a surgically implanted catheter leading to the patient's peritoneal space, and at its other end to a "Y" fitting connected to a tube assembly from the exchange fluid bags and to a tube assembly leading to the drain bags. The fluid exchange bag and the drain bag tube assemblies are easily inserted into and controlled by zero loading force, normally closed, solenoid control valves. A laptop microcomputer serves as a controller to convert differential weights into volumes, activate the control valves, time the fill, dwell and drain portions of each cycle, detect and alarm malfunctions, and record all patient information concerning each cycle. The controller permits customizing of the cycles to the patient, has both manual and automatic modes of operation, and provides options to the patient in restarting interrupted cycles.

13 Claims, 5 Drawing Sheets

PORTABLE PERITONEAL DIALYSIS CYCLER

TECHNICAL FIELD

The invention relates to a portable, gravity-type, peritoneal dialysis cycler, and more particularly to such a cycler provided with a differential weighing system, improved electrically actuated control valves, and a standard laptop computer control unit therefor.

BACKGROUND ART

Peritoneal dialysis is the process by which an exchange fluid is periodically introduced into and removed from the peritoneal space of a patient by means of a surgically implanted catheter. The process enables the removal of body waste when the normal kidney functions are inoperative. The process comprises a fill, dwell and drain cycle which is normally repeated a number of times each day, often while the patient is asleep. As a consequence, the device which controls and performs the dialysis process is generally referred to in the art as a "cycler".

Prior art cyclers have been installed both in hospitals and in homes, intended for permanent use in a fixed location. Prior art cyclers are generally characterized as being bulky, noisy in operation, and generally quite expensive.

Some patients, of necessity or by choice, must travel while still meeting the daily requirements of peritoneal dialysis. Prior art workers have devised a limited number of "portable" cyclers. These cyclers, however, are still characterized by being bulky, unnecessarily complex and expensive.

The present invention is directed to a truly portable, light-weight cycler of approximately 35 pounds and capable of fitting into a standard traveling case. The cycler is relatively inexpensive since the majority of its components are "off-the-shelf" elements, as will be set forth hereinafter.

The cycler is simple in construction, reliable, and easy to use. The cycler employs standard sterilized tubing sets and standard exchange fluid bags and drain bags. A differential weighing system is employed, requiring only one scale comprising a load cell and its associated electronic circuitry. A laptop microcomputer is employed as the central control unit and enables customizing of the cycles for the individual patient, comprehensive data logging, both automatic and manual control, and a number of options at the time of restart of an interrupted cycle.

DISCLOSURE OF THE INVENTION

According to the invention, there is provided a peritoneal dialysis cycler of the gravity type. The cycler comprises a detachable base and a vertical stand. The stand is shiftable between a collapsed state and an extended state, and is mountable on the base. The stand supports a single load cell from which a pair of exchange fluid bags are suspended above the level of the usually recumbent patient, and from which a pair of drain bags are suspended below the level of the patient. The load cell is connected to the electronic circuitry of the scale. A sterile plastic tubing set is provided comprising a first tube connected at one end to a surgically implanted catheter leading to the patient's peritoneal space and at its other end to a fitting connected both to a tube assembly from the exchange fluid bags and to a tube assembly leading to the drain bags. The tube assembly from the exchange fluid bags has a portion which is easily insertable into a solenoid actuated on-off valve. The valve normally pinches the tube assembly portion to a closed position. When energized, the solenoid valve will release the tube portion to an open position. The tube assembly leading to the drain bags is similarly provided with a normally closed solenoid valve. The two solenoid control valves are provided with special rotatable top elements enabling the location therein of the tube assembly portions with a minimum of manipulation and dexterity required.

The cycler is provided with a controller in the form of a laptop computer which controls each cycle and records all pertinent information concerning each cycle. The computer receives and interprets signals from the electronic scale and appropriately energizes and deenergizes the solenoid valves. The controller determines the amount of fluid infused into the patient and drained from the patient by a differential weighing system to be described hereinafter. The controller enables customizing of the cycles to the individual patient, as both manual and automatic modes of operation, and provides options to the patient in restarting interrupted cycles.

DETAILED DESCRIPTION OF THE INVENTION

Figure 1:
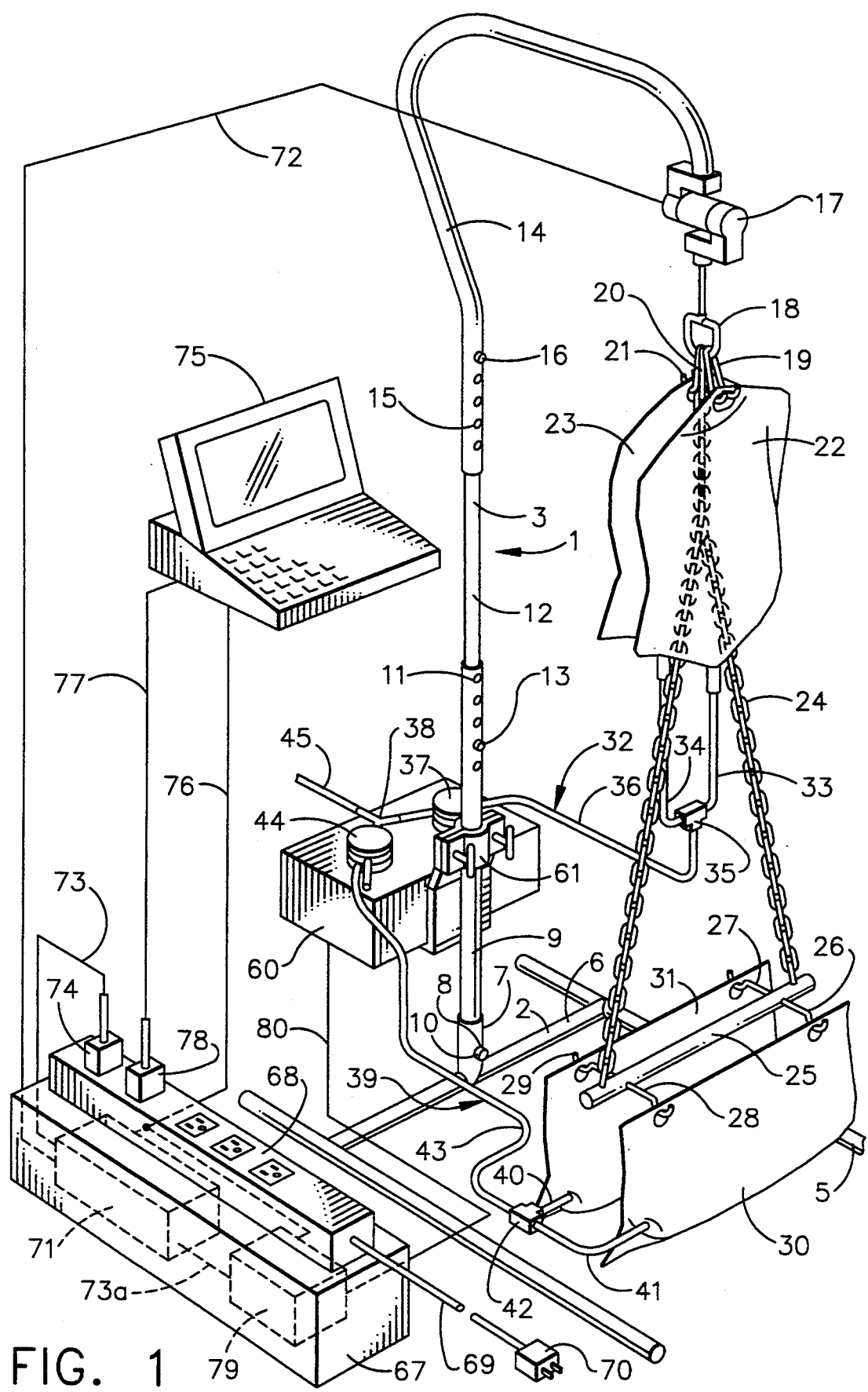
FIG. 1 is a simplified, isometric view of the cycler of the present invention.

Reference is first made to FIG. 1 wherein the cycler of the present invention is illustrated in its entirety in simplified form. The cycler comprises a vertical stand, generally indicated at 1. The stand comprises a base 2 and an upstanding, vertical portion 3. The stand 1 may be made of any appropriate material and in any appropriate manner, so long as it is sturdy, light weight, and can be easily assembled and disassembled for convenient transport. In an exemplary embodiment, the base 2 in FIG. 1 is illustrated as being made up of a pair of tubular members 4 and 5, joined together by an additional tubular member 6 to form a substantially "H" shaped configuration. The tubular member 6 has affixed thereto an upstanding tubular member 7. The tubular member 7 is provided with a perforation 8.

The upstanding, vertical portion 3 of the stand 1 comprises a first tubular member 9. The tubular member 9 is of such diameter as to be receivable within the tubular member 7 with a telescoping fit. The tubular member 9 is provided near its lower end with a conventional spring detent-type snap latch 10, releasably engagable in perforation 8 of tubular member 7. The upper portion of tubular member 9 has a plurality of perforations 11 similar to perforation 8. An additional tubular member 12 has a lower end telescopically receivable within the tubular member 9. The lower end of tubular member 12 is provided with a spring detent-type snap latch 13 releasably engagable in any one of perforations 11 in tubular member 9. Finally, there is a hook-shaped tubular member 14, the lower end of which is provided with a plurality of perforations 14. The upper end of tubular member 12 is telescopically engagable in the lower end of tubular member 14 and is provided with a spring detent-type snap latch 16 engagable in any one of perforations 15.

It will be apparent from FIG. 1 that the base 2 of the vertical stand 1, and the elements which make up the upstanding portion 3 can be easily assembled and disassembled by simple manipulation of the snap latches 10, 13 and 16. The telescoping engagements between the tubular members 7, 9, 12 and 14 enable easy height adjustment of the stand 1 to meet the requirements as will be set forth hereinafter.

The free end of the hook-shaped tubular member 14 has a load cell 17 affixed thereto. The load cell 17 has a downwardly depending loop element 18 on which are mounted three hooks 19, 20 and 21. Each of the outermost hooks 19 and 21 supports an exchange fluid bag 22 and 23, respectively. The intermediate hook 19 supports a chain assembly 24. The lower ends of chain assembly 24 are affixed to and suspend a horizontal bar 25. The horizontal bar 25 is provided with diametrically opposed pairs of hooks 26–27 and 28–29. The hooks 26 and 28 support a first drain bag 30. The hooks 27 and 29 support a second drain bag 31. Normally, when the cycler is in use, the patient is in a recumbent position. This is not required, however, and the patient can be in a seated position, for example. The vertical adjustability of the stand 1 is important since the exchange fluid bags 22 and 23 must be above and the drain bags 30 and 31 must be below the peritoneal space of the patient, since the cycler is of the gravity type.

The exchange fluid bags 22 and 23 are provided with a tube assembly generally indicated at 32. The tube assembly 32 comprises a pair of short tubes 33 and 34, each attached to one of the exchange fluid bags 22 and 23 in a conventional manner. The short tubes 33 and 34 are attached as at 35 to a single exchange fluid tube 36. The single exchange fluid tube 36 is engaged by a control valve 37 (as will be described hereinafter) and is thereafter connected to a "Y" fitting 38.

In a similar fashion, the drain bags 30 and 31 are provided with a tube assembly, generally indicated at 39. The tube assembly 39 comprises a pair of short tubes 40 and 41, each leading from one of the drain bags 30 and 31, respectively. The short tubes 40 and 41 are connected as at 42 to a single drain bag tube 43. The single drain bag tube 43 is engaged by a control valve 44 (to be described hereinafter) and is ultimately connected to the "Y" fitting 38.

Also connected to the "Y" fitting 38 is a single tube 45 which leads to the patient (not shown). The free end of tube 45 is attachable to a surgically implanted catheter leading to the patient's peritoneal space, as is well known in the art.

Figure 2:
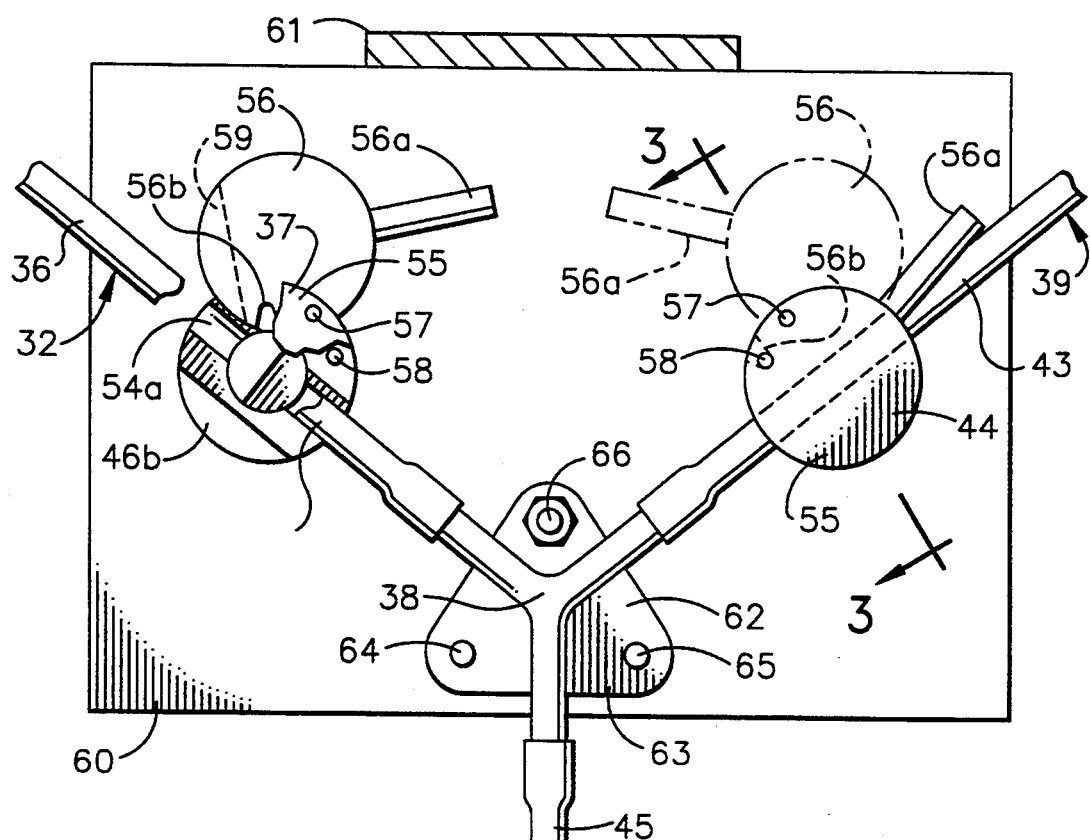
FIG. 2 is a fragmentary plan view of a sterile tubing set and the solenoid on-off valves therefor.

The valves 37 and 44 are substantially identical. The valves 37 and 44 are shown in FIG. 2 and the valve 44 is shown in cross section in FIG. 3. A description of valve 44 may stand as a description of valve 37. Like parts of valve 37 have been given the same index numerals as the same parts of valve 44. The valve 44 comprises a valve body 46 having two portions 46a and 46b joined together by a plurality of bolts, two of which are shown at 46c. The body 46a has a vertical bore 47 formed therein. The bore 47 terminates in an enlarged bore portion 48 containing a cylindrical electrical coil 49. A plunger or core 50 is mounted within bore 47 and the coil 49 and is axially shiftable therein. The lower end of the core 50 abuts a compression spring 51. The lower end of compression spring 51, in turn, abuts the bottom of bore 47.

The upper end of the core 50 is threaded and engaged thereon there is a threaded anvil or nose 53 which is shiftable with core 50 within bore 54 in body portion 46b. The upper end of bore 54 is intersected by a shallow groove 54a, the purpose of which will be apparent hereinafter.

The valve body 46 is provided with a cap 55 which is spaced upwardly therefrom. Between the valve body 46 and its cap 55, there is a rotatable insert 56. The insert 56 is rotatable about pivot pin 57. The rotatable insert 56 is provided with a handle 56a.

The cap 55 is supported above valve body portion 46b by pivot pin 57 which is frictionally engaged in bores in cap 55 and valve body portion 46b, passing through a bore in insert 56 with clearance. The cap 55 is further supported by a second pin 58 frictionally engaged in bores in valve body portion 46b and cap 55.

The insert 56 is rotatable about pivot pin 57 between a closed position wherein it lies fully between the valve body portion 46b and valve cap 55 and an open position wherein a majority of the insert 56 lies outside the valve body 46 and cap 55, exposing the groove 54a. The insert 56 is provided with a notch 56b. The pin 58 abuts within notch 56b to determine the closed position of insert 56. The insert 56 of valve 37 is shown in this open position in solid lines in FIG. 2. A portion of the valve cap 55 of valve 37 has been broken away in FIG. 2 to expose the groove 54a. When the rotatable insert 56 of valve 37 is in the open position shown in FIG. 2, the patient can locate a portion of the tube 36 of tube set 32 in the groove 54a. The rotatable insert 56 may then be rotated in a counterclockwise direction (as viewed in FIG. 2) by its handle 56a to its closed position wherein it covers that portion of tube 32 located within groove 54a and maintains the tube within the groove. It will be understood that the rotatable insert 56 of valve 44 operates in precisely the same manner, with respect to the tube 43 of tube set 39 so as to lock a portion of the tube 43 within the groove 54a (see FIG. 3) or release the tube therefrom.

Figure 3:
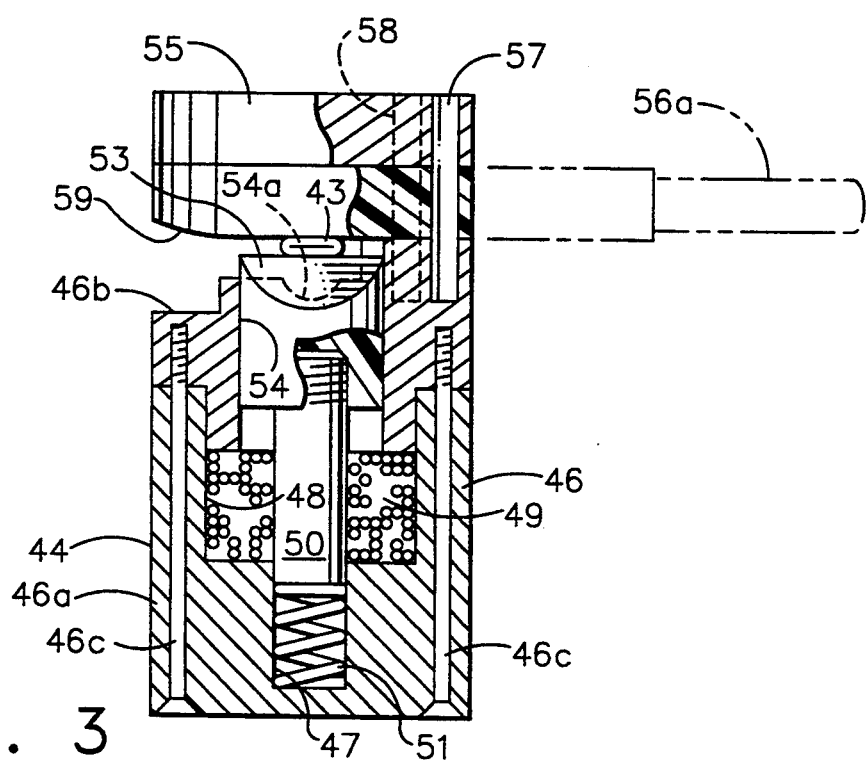
FIG. 3 is a cross sectional view taken along section 3—3 of FIG. 2.

As is most clearly shown in FIG. 3, the core 50 is normally urged to its uppermost position (as shown in FIG. 3) by compression spring 51. The nose portion 53 of the core 50 pinches or collapses the adjacent portion of tube 43 to a closed position. The undersides of the rotatable inserts 56 of valves 44 and 37 are chamfered as at 59 so that it requires almost zero force on the part of the patient to insert and lock the sections of tubes 32 and 43 in their respective grooves 54a in the valves 37 and 44.

Returning to FIG. 3, when the coil 49 is energized, the core 50 will shift downwardly against the action of compression spring 51. This will enable the tube 43 to assume its fully round, open cross section within groove 54a. It will be understood that the core of valve 37 will operate in precisely the same way. Thus the cores of valves 37 and 44 will normally act to maintain their respective tubes 32 and 43 in a pinched or closed condition. When the valve coils are energized, their respective cores will move downwardly, opening the tubes 32 and 43, respectively.

It will be apparent from FIGS. 1 and 2 that when valve 37 is open and valve 44 is closed, exchange fluid will pass from exchange fluid bags 22 and 23 through the tube set 32 and the tube 45 to the peritoneal space of the patient. Similarly, when valve 37 is closed and valve 44 is open, exchange fluid will flow from the peritoneal space of the patient through tube 45 and tube set 39 into drain bags 30 and 31. As a consequence, valve 37 constitutes an input control valve and valve 44 serves as the drain control valve.

The valves 37 and 44 are mounted in a valve support 60. As a matter of convenience, the valve support 60 may be adjustably affixed to tubular member 9 of stand 1 by a conventional clamp assembly 61.

As shown in FIG. 2, the "Y" fitting 38 has an integral web or plate-like portion which may have any appropriate peripheral configuration. In the embodiment illustrated, the web 62 is shown as being substantially triangular. The valve support 60 has a pair of upstanding pins 64 and 65 and an upstanding threaded stud 66. The "Y" fitting web 62 is provided with perforations through which the pins 64 and 65 and the threaded stud 66 extend. A nut screwed upon the threaded stud 66 will maintain the "Y" fitting in place on the valve support 60.

The cycler of the present invention may be used with conventional, readily available, sterilized tubing sets as known in the art. Some of these tubing sets are provided with a "X" shaped fitting in place of the "Y" shaped fitting 38, providing a second tube to the patient. Since such a second tube is not required in the present cycler, the "X" fitting can be removably affixed to the valve support 60 and the extra tube can simply be clamped off.

Reference is again made to FIG. 1. A rectangular box 67 has mounted on its upper surface a conventional outlet strip 68. The outlet strip 68 is provided with a conventional cord 69 and plug 70 by which it may be connected to an ordinary source of 120 volts AC. Within the box 67 there is diagrammatically indicated at 71 a scale interface circuit and an associated DC power supply. The scale interface circuitry and power supply and the load cell 17 are interconnected by cable 72. The scale interface circuitry and DC power supply are, themselves, connected to outlet strip 68 by cable 73 and plug 74. The output of the scale interface circuitry is an RS-232 serial output which is connected by cable 76 to a serial input RS-232 interface of a laptop microcomputer 75. The laptop microcomputer 75, itself, is connected to outlet strip 68 by cable 77 and plug 78.

The box 67 also contains a valve interface switching circuit and DC power supply diagrammatically indicated at 79. The valve interface switching circuit and DC power supply assembly 79 is connected to the outlet strip 68 by means of plug 74, cable 73 and cable 73a. Low voltage valve control command signals (in the range of 0–5 VDC) are received by the valve interface switching circuit 79 from the laptop microcomputer 75 via cable 76. The low voltage signals are converted into higher voltage and current signals by the valve interface switching circuit 79, sufficient to actuate the control valves 37 and 44. These higher voltage valve control commands are received by the valves 37 and 44 from the valve interface switching circuit 79 via cable 80.

A personal computer could be used in lieu of laptop microcomputer 75, however, a laptop-type microcomputer is preferred for any portable applications. Laptop microcomputer 75 can be any standard laptop microcomputer having at least one disk drive, and having at least 256 Kbytes of RAM (Random Access Memory). The Tandy Model 1100FD laptop microcomputer has successfully executed this application program, and preferably includes a floppy disk drive which handles a 720 Kbyte floppy disk. The laptop microcomputer 75 is programmed in a standard computer language, such as industrial floating-point BASIC, to convert differential weights to volumes, to activate the control valves 37 and 44, to time the fill, dwell and drain intervals of a cycle, to detect and alarm malfunctions such as the patient lying on the tubing and obstructing the fluid flow, logging all events and the like. The use of a microcomputer and standard language enables flexibility of customizing the cycles to specific patient requirements and enables restarting options for cycles which have been interrupted.

The input and drain control valves 37 and 44, having the special construction described above to minimize the effort of locating the tubes 36 and 43 within the valves, are otherwise conventional, being solenoid valves actuated by 12 volts DC.

The valve interface switching circuit 79 contains electronic pulse shaping circuitry which converts the signals from the laptop microcomputer 75 to a special waveform which provides an initial high energy component to assure rapid and complete opening of the valves, and a subsequent low energy state sufficient to maintain the valves in their open state, but reducing the dilatorious effect of heat on the electrical components of the solenoids. The initial high energy waveform is preferably at 15 VDC, and the subsequent steady-state low energy level is preferably at 12 VDC, when using this particular valve. This assures longer life and more reliable performance. The valves 37 and 44 are modified versions of pinch valve solenoids manufactured under the designation N-1367-91 by Cole Palmer, of Chicago, Ill.

The load cell may be of any appropriate type. Excellent results have been achieved with a load cell designated SENS-60036-050, manufactured by Sensortronic, Inc., of Covina, Calif. The scale interface circuitry 71 constitutes a Penn-6300 SMART BOX, manufactured by Pennsylvania Scale Company of Leola, Pa. The load cell 17 produces an electrical current in proportion to the weight attached thereto. The scale interface circuitry 71 converts the load cell current to digital values equal to the weight attached. These digital values are communicated as a serial message to the laptop microcomputer 75 via cable 76.

Figure 6:
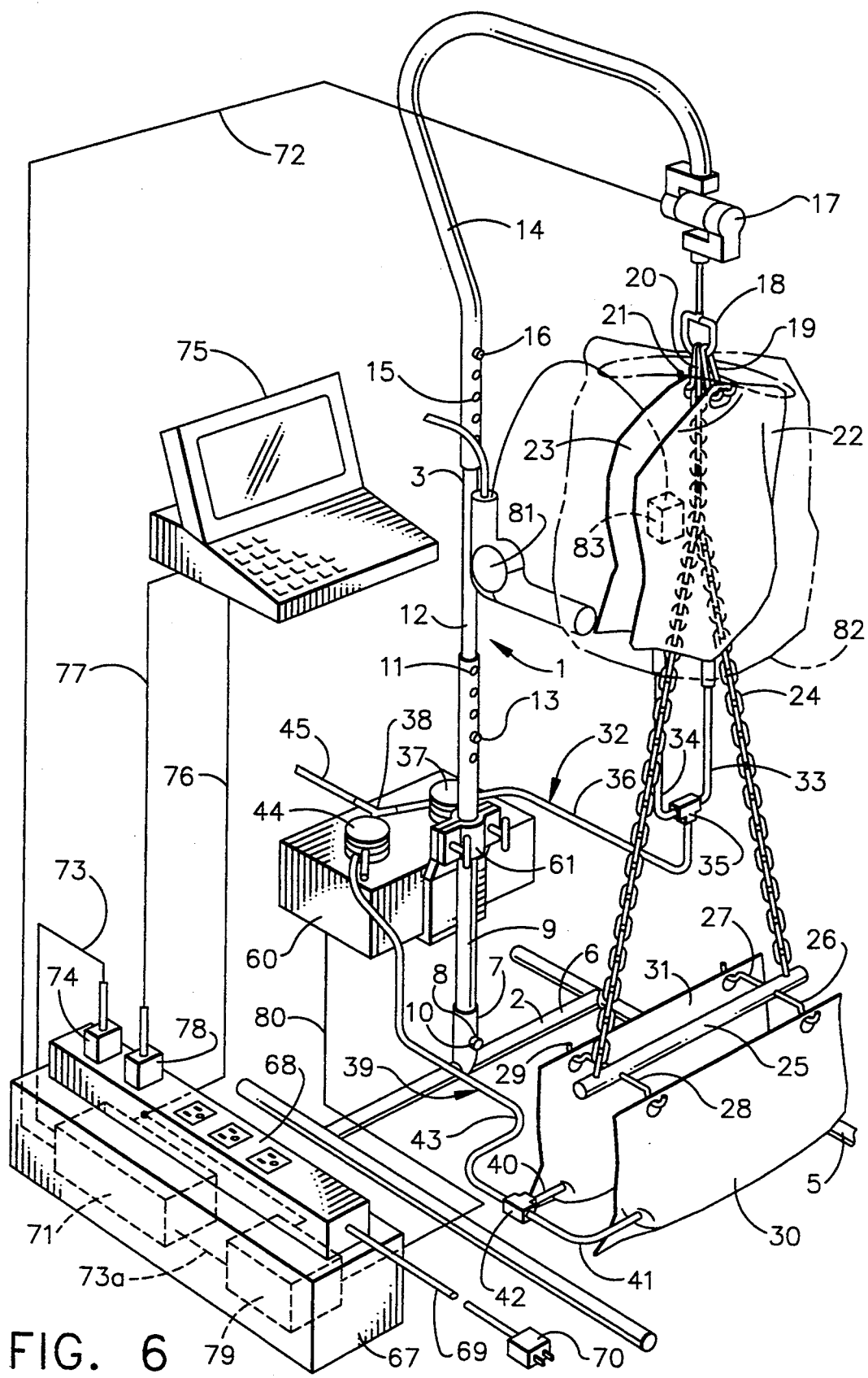
FIG. 6 is an isometric view of the cycler of the present invention provided with means to heat the exchange fluid.

It is within the scope of the invention to provide means for heating the exchange fluid. Any appropriate means and method can be used. In FIG. 6, the cycler is shown provided with a hot air blower 81 connected to a shroud 82 located about the exchange fluid bags 22 and 23. The shroud has an opening at the bottom to accommodate chain assembly 24. The shroud 82 is also open at the top to allow adequate flow of the warm air about exchange fluid bags 22 and 23. A thermostat 83 may be located between exchange fluid bags 22 and 23 to regulate the blower 81. The blower 81 can be arranged to be turned on and off at appropriate times in each cycle by the microcomputer 75, if desired.

The cycler having been described in detail, its operation can now be set forth.

Figure 4:
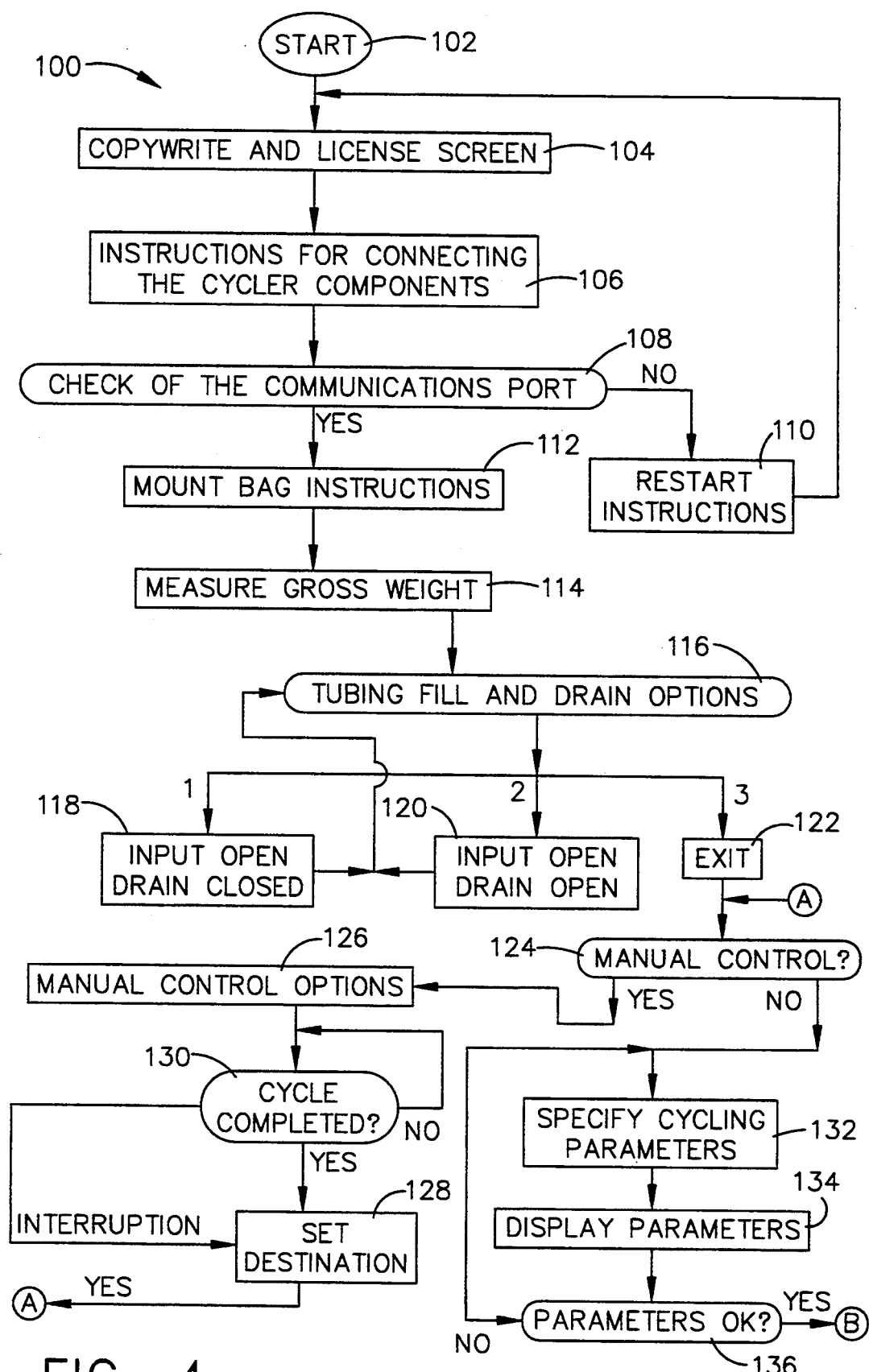
FIGS. 4 and 5 illustrate a flow chart for the operation of the cycler of the present invention.
Figure 5:
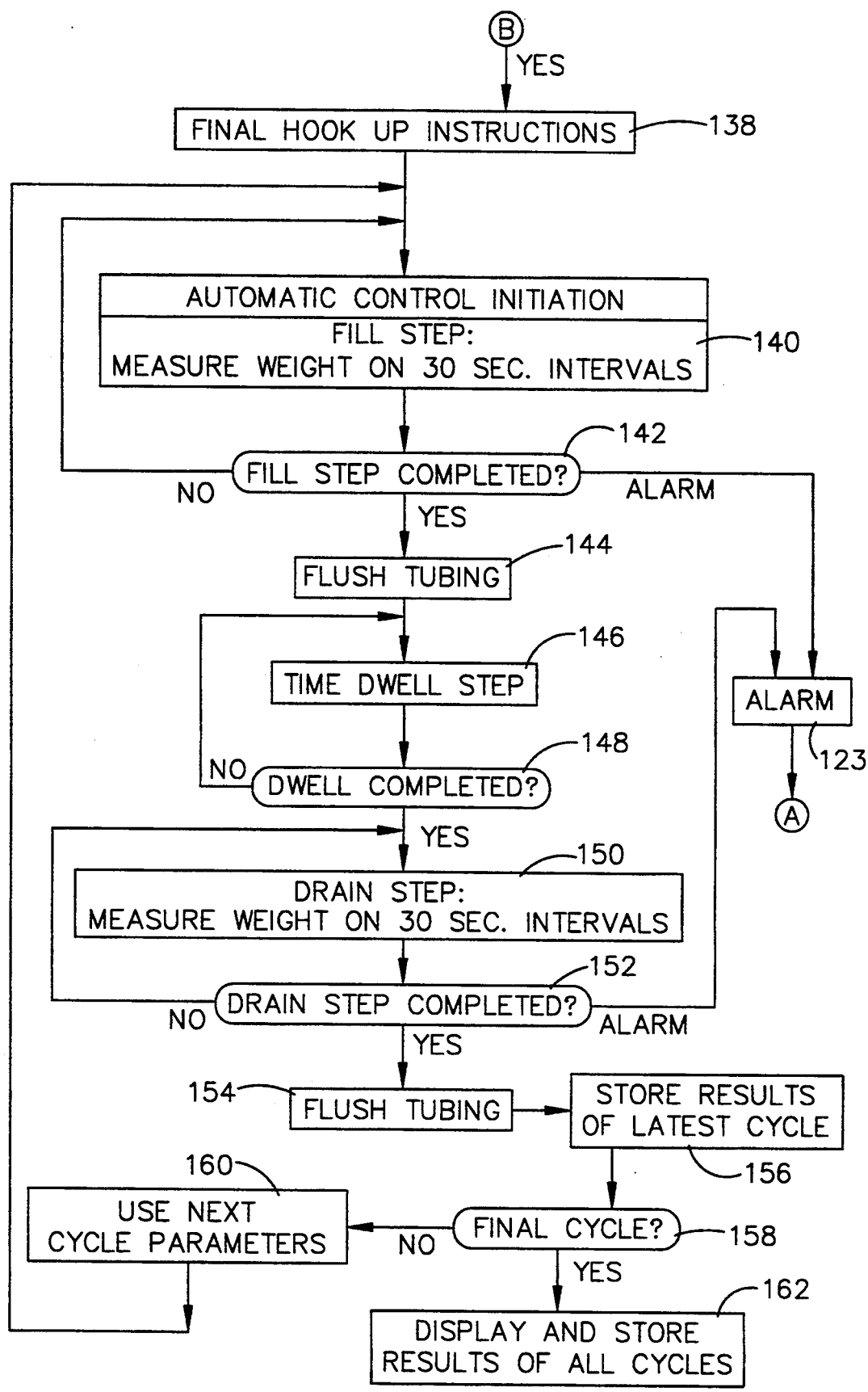

FIGS. 4 and 5 contain a flow chart 100 which describes the various steps that the computer program executes, under the control of the laptop microcomputer 75. As described above, laptop microcomputer 75 acts as a central control unit for the entire system, and determines when to open or close either of the two control valves 37, 44.

When laptop computer 75 first starts to execute the computer program, as depicted by the index numeral 102 on FIG. 4, it proceeds to display a copyright notice and conditions for licensing the use of this computer program, via function block 104. After this occurs, function block 106 displays the instructions for connecting the various components of the portable peritoneal dialysis cycler. These instructions include connecting the proper electrical wires to the load cell 17, to the scale interface circuitry and D.C. power supply 71, to the valve interface switching circuit and D.C. power supply 79, and to the control valves 37, 44. In addition, the instructions will inform the patient to connect certain signal wiring between laptop microcomputer 75 and the scale interface circuitry and D.C. power supply 71, and between laptop computer 75 and the valve interface switching circuit and D.C. power supply 79.

The computer program now arrives at decision block 108 in which the communications port is tested for proper operation. If the communication port fails its test, then the logical flow proceeds to function block 110 which provides restart instructions to the patient, and the logical flow is directed back to the start of the computer program at the initialization block 102. If, on the other hand, the communications port successfully passes its test, the logical flow proceeds to function block 112. During the check of the communications port, at decision block 108, the laptop microcomputer 75 displays the following message:

CHECKING THE OUTPUT PORT AND SCALE. IF "DEVICE TIMEOUT" APPEARS, TURN SYSTEMS BOX OFF THEN ON. THEN PRESS THE CONTROL AND BREAK KEYS SIMULTANEOUSLY. THE CONTROL KEY IS THE LEFT KEY ON THE BOTTOM ROW AND THE BREAK KEY IS 3RD FROM THE RIGHT ON THE TOP ROW. THEN TYPE RUN TO RESTART.

The communications port is connected to the serial port of the scale interface circuitry and D.C. power supply 71. The laptop microcomputer 75 sends a brief message via its serial communications port, and waits to receive an acknowledgement message from the serial port of the scale interface circuitry and D.C. power supply 71. If the proper response is received by laptop microcomputer 75 within a short time period, then decision block 108 allows the logical flow to proceed to function block 112. Otherwise, the logical flow is directed to function block 110.

At function block 112, the patient is instructed as to how to mount the bags and to connect the plastic tubing for the portable peritoneal dialysis cycler, by displaying the following messages:

MOUNT DRAIN BAGS, CLAMP FILL, PATIENT AND DRAIN TUBES.
SET KEYBOARD CAPS ON.
PRESS ENTER KEY.

After the exchange fluid bags 22, 23 and the drain bags 30, 31 have been properly mounted and had their tubing hooked up, the logical flow proceeds to measure the gross weight of all of the bags and fluids, via function block 114. After this weight has been stored in the computer's Random Access Memory, decision block 116 of the computer program presents certain tubing fill and drain options. At this point, the laptop computer's screen displays the following message:

VALVE CHECKING AND TUBING FILL OPTIONS
 1. FILL OPEN, DRAIN CLOSED (CHECK FLOW OR FILL CATHETER TUBING)
 2. FILL OPEN, DRAIN OPEN (FLUSH ALL TUBING)
 3. EXIT THIS OPTION

To properly respond to the options presented to the patient, the patient merely types in a number in the range of 1 through 3, and presses the Enter key. If choice number "1" is selected, the "Fill" control valve 37 will be opened and the "Drain" control valve 44 will remain closed. This option is used to fill the tubing with fluid up to the catheter, and can also be used to check flow. These operations are controlled by function block 118 of the flow chart 100.

If option number "2" is selected by the patient, then both of the control valves 37, 44 are opened, under the control of function block 120. While in this condition, the system can flush all of the tubing, including to the patient, and from the patient through the drain; the patient can also check for leakage.

Once the patient has finished using either options "1" or "2" or does not desire to use either option, then the patient can select the number "3" to exit this portion of the computer program, under the control of function block 122. At this time, the laptop microcomputer's monitor displays the following message: "DO YOU WISH MANUAL CONTROL?", via a decision block 124. At this point, the patient is to either enter the letter Y (for YES), or the letter N (for NO). If the above patient response is Y, the flow chart proceeds to function block at which time the laptop microcomputer's monitor displays the following message:

SELECT NEXT ACTION TO BE DONE
 1. FILL
 2. DWELL
 3. DRAIN
 4. FLUSH
 5. RETURN TO NEXT FULL CYCLE
ENTER THE NUMBER CHOSEN >

Each of the above options performs a different function, and decision block 130 determines whether the requested cycle has been completed or not. If the cycle has not yet been completed, the control flow continues to execute the desired cycle. On the other hand, if the cycle is either interrupted or if it has been successfully completed., the logical flow proceeds to a function block 128 known as the "Set Destination" screen, which displays the following message:

PLEASE SELECT WHAT YOU WANT TO FOLLOW THE COMPLETION OF THE ACTION JUST SPECIFIED.
 1. COMPLETE THE INTERRUPTED CYCLE
 2. SPECIFY ENTIRE NEW CYCLING PROGRAM
 3. RETURN TO MANUAL CONTROL
ENTER THE NUMBER CHOSEN >

If the previous cycle was interrupted for any reason, and the patient desires that cycle to be completed, the patient would type the number "1" and presses the Enter key. If the patient would rather return to manual control, the patient would type the number "3" and a carriage return. The last choice allows the patient to specify an entirely new cycling program by entering the number "2" and a carriage return.

If the patient decides not to enter manual control at decision block 124, the control flow proceeds to function block 132 where the patient may specify cycling parameters in preparation for an automatically controlled dialysis procedure. At this time, the laptop microcomputer's monitor displays the following message:

AUTO-CYCLE PARAMETERS

PLEASE ENTER THE REQUESTED INFORMATION

STARTING CYCLE NO . . .
NUMBER OF CYCLES DESIRED . . .
SPECIFY INPUT VOLUME, FILL, DWELL AND DRAIN TIMES FOR EACH CYCLE.
CYCLE NO . . .
INPUT VOL(L) . . .
FILL TIME . . .
DWELL TIME . . .
DRAIN TIME . . .

Under the control of function block 132, the patient may specify the number of dialysis cycles to be performed, along with all of the important parameters for each cycle, such as Fill Time, Dwell Time, and Drain Time. Typical values for these parameters are as follows:

Number of Cycles: 5
Input Volume: 2 liters (per cycle)
Fill Time: 15 minutes
Dwell Time: 80 minutes
Drain Time: 25 minutes
Total Time: 2 hours per cycle The patient may specify all of these parameters before the start of the cycling process. The system is designed so that the patient may specify in advance all of this information, which defines a process that will require approximately ten hours for completion, under automatic control. After the process is started, the patient may go to bed and sleep through the entire process. The only reason the process would stop execution is if a flow restriction is detected, at which time an audible alarm would sound, thereby awaking the patient.

After the cycling parameters have been specified by the patient under the control of function block 132, the parameters are then displayed via function block 134. The patient is now asked if the parameters which have been entered are correct or not, under the control of decision block 136. If the answer is NO, then the logical flow returns to the input screen before the first cycle and awaits the input of correct data under control of function block 132. If the answer is YES, then the logical flow proceeds from FIG. 4, at the letter "B", to FIG. 5, at a corresponding letter "B", continuing to function block 138, which provides the patient with final instructions for hooking up the system. Such instructions are as follows:

PLEASE CONNECT THE INPUT TUBE TO PATIENT.
PLEASE OPEN ALL CLAMPS.
THE SYSTEM IS NOW READY FOR PRESET CYCLING.
PRESS ENTER KEY.

After the final hook-up has been completed, the patient presses the Enter key, thereby enabling the system to proceed with the dialysis cycling, and the logical flow arrives at function block 140, which is the Fill Step. During the Fill Step, the fill control valve 37 is open and the drain control valve 44 remains closed, so that fluid from the infusate bags (exchange fluid bags 22 and 23) can enter the patient. At thirty (30) second intervals, the weight is measured and compared to the initial value to determine the amount of differential volume loss in the fill procedure. The above typical Fill Step was specified at fifteen (15) minutes for completion. However, at a time equalling two-thirds of the specified fill time (10 minutes in a typical example), the volume is checked for a transfer of at least 50% of the specified volume, or an alarm will occur. If an alarm condition occurs, caused by an obstruction to the patient tubing, an audible alarm sounds and the control valves 37 and 44 are de-energized and closed so that no fluid can move in the system. The monitor displays the following screen:

PERFORMANCE HISTORY TO THE TIME OF THE ALARM

| CYCLE NUMBER | FLUID IN | FLUID DRAINED |
|---|---|---|
| . . . | . . . | . . . |
| . . . | . . . | . . . |
| . . . | . . . | . . . |
| FOR CYCLE NO. (THE CYCLE INTERRUPTED) | | |
| START VOL. | . . . | |
| CURRENT VOL. | . . . | |
| ELAPSED TIME | . . . | |
| TIME ALARM WAS TERMINATED | . . . | |
| VOL. TRANSFERRED IN THIS CYCLE | . . . | |

PLEASE REVIEW THIS INFORMATION AND DECIDE HOW YOU WISH TO CONTINUE THE CYCLE. THEN PRESS THE ENTER KEY.

As the fluid exits the fluid exchange bags mounted above the patient, and enters the patient's peritoneal space, the gross weight, as measured by the load cell 17, will decrease by a certain amount. To measure the weight, both of the control valves 37 and 44 are momentarily closed for approximately one second.

After the weight is measured upon each thirty (30) second interval, decision block 142 determines whether or not the Fill Step has been completed. The actual weight (volume) loss is compared to the desired weight (volume) loss for a nominal fill, and once that actual weight loss has equalled or exceeded the desired amount, then decision block 142 determines that the Fill Step has been successfully completed. At that point the system continues to the flush tubing step, under control of function block 144.

On the other hand, if at the end of the fill time (as defined earlier by the patient), the nominal amount of weight has not transferred out of the exchange fluid bags 22 and 23, then the system will decide that a flow restriction has occurred, and an audible alarm will sound to wake up the patient. The likely cause of this flow restriction is where the patient would happen to roll over and lay upon the tubing through which the liquid is attempting to flow into the patient's peritoneal space. By awakening the patient, the situation can be rectified. As before, once the alarm condition occurs, the valves 37 and 44 are de-energized and close so fluid cannot move in the system. The monitor displays the same alarm screen depicted above.

The logical flow of the computer program will proceed from decision block 142 to the alarm routine, at function block 123. The logical flow will then continue from function block 123, to the letter "A" on FIG. 5, then back to FIG. 4, at a corresponding letter "A".

After the patient decides how to further proceed, pressing the "Enter" key returns the logic flow to the manual control decision block 124. Under normal circumstances, the patient will specify NO to the manual control option, thereby reentering the automatic cycle, wherein the patient may specify the cycling parameters again, under control of function block 132. During the alarm routine, the laptop computer's monitor displays the current status of the automatic cycling process. With this information, the patient can intelligently decide what to do insofar as reentering either the manual or automatic control procedures.

Once the Fill Step has been successfully completed, the logical flow arrives at function block 144 wherein the tubing is flushed. The flush tubing step opens both of the control valves 37 and 44 for approximately one second, thereby flushing the system and eliminating any back-flow from the drain and removing any bacteria that may have formed in the meantime.

After the tubing has been flushed, the logical flow arrives at the Time Dwell Step under control of function block 146. As discussed above, a typical time period for the Dwell Step is eighty (80) minutes. During this time, both of the control valves 37, 44 are closed off, thereby permitting the fluid to be retained within the peritoneal space of the patient. During this eighty (80) minute period, the patient cannot do anything wrong to generate an error or other alarm, because there is no flow through any of the tubing during this period. Decision block 148 determines whether the Dwell Step has been completed or not, and is strictly driven by elapsed time. Once the Dwell Step is completed, the logical flow continues to the Time Drain Step, under the control of function block 150. During the Drain Step, the fill (input) valve 37 remains closed, and the drain control valve 44 is opened. This allows the ultrafiltrate to leave the patient's peritoneum space and enter into the drain bags 30, 31.

A typical time interval for the occurrence of the Drain Step is twenty-five (25) minutes. At a time approximately two-thirds into the Drain Step (i.e., approximately sixteen (16) minutes for a twenty-five (25) minute Drain Step), both of the control valves 37 and 44 are momentarily closed off and the weight is measured. At this moment, at least one-half of the fluid by weight must have transferred from the peritoneal space into the drain bags 30 and 31, or an alarm will be generated. Decision block 152 makes this determination, and if a flow restriction has occurred, an audible alarm will sound, the laptop microcomputer's monitor will display the current status, and the logical flow will proceed to the alarm routine, designated as function block 123. As before, the logical flow will continue from function block 123, to the letter "A", then back to FIG. 4 at the letter "A". After the patient decides how to further proceed, pressing the "Enter" key returns the logic flow to the manual control decision block 124.

In case of an alarm condition caused by an obstruction to the patient tubing, an audible alarm sounds and the control valves 37 and 44 are de-energized and closed so that no fluid can move in the system. The monitor displays the same alarm screen depicted above.

Assuming that the above alarm condition does not occur, at the end of the specified time (e.g., twenty-five (25) minutes), decision block 152 will determine that the Drain Step has been completed, and the logical flow will continue to the flush tubing step, at function block 154. At this time, the system will open both control valves 37, 44 for approximately one second to flush the system, thereby eliminating back-flow from the drain and removing any bacteria.

After the flush tubing step has occurred, the logical flow proceeds to function block 156 at which time the results of the latest cycle are stored onto the disk of the laptop microcomputer 75. The results include the fill weight and drain weight of the latest cycle. It is important that this information is stored at the end of each of the cycles in case electrical power is lost and the system shuts down during a subsequent cycle. By storing the results at this time, there will be at least a certain amount of data retained on disk, regardless of a power failure.

At this time, decision block 158 determines whether or not the final cycle has just been completed. If the answer to this question is NO, then the logical flow proceeds to function block 160 which instructs the laptop computing system to use the parameters which have been entered for the cycle that will be completed next. The logical flow then proceeds to function block 140, which is the Fill Step of the next cycle to be completed.

If the final cycle has just been completed, as determined by decision block 158, then the logical flow proceeds to function block 162 at which time the results of all of the previous cycles are stored on disk and the monitor displays such results. Not only are the individual fill weights and drain weights displayed, but the total fill and drain weights are displayed as well. The patient can easily determine if he or she needs to replenish any body fluids, if necessary, to prevent dehydration.

An example of the screen which is displayed on the monitor by function block is as follows:

| DIALYSIS SESSION RESULTS (ALL VALUES IN LITERS) | | |
| --- | --- | --- |
| CYCLE NO. | INPUT | DRAIN DIFFERENCE |
| ... | ... | ... |
| ... | ... | ... |
| ... | ... | ... |
| TOTAL INPUT FLUID | | ... |
| TOTAL DRAIN FLUID | | ... |
| BODY FLUID REMOVED | | ... |

Each of the appropriate steps has been described in detail for the automatic cycling procedure. The very same steps can be accomplished in a similar manner while under manual control. As discussed above, function block 126 provides the patient with the manual control options, and those options specify the same Fill, Dwell, Drain, and Flush steps as are available in the automatic cycle.

As discussed above, an optional electric air heater 81 (see FIG. 6) can be used to preheat the liquid stored in the exchange fluid bags 22, 23. The air heater 81 would be energized during any fill operation, in which fluid is being infused into the user's peritoneal space, whether under manual or automatic control. In this way, the fluid entering the patient's body will have been heated to near body temperature.

Modification may be made in the invention without departing from the spirit of it.

I claim:

1. A peritoneal dialysis cycler of the gravity type for use with a patient, comprising:
   (a) a stand having a base portion and an upstanding vertical portion;

(b) a single load cell attached to and supported by said stand;

(c) at least one fluid exchange bag supported by said load cell;

(d) at least one fluid drain bag supported by said load cell;

(e) a fill control valve;

(f) a drain control valve;

(g) a first electrical power supply and interface circuit electrically connected to said fill and drain control valves to convert low voltage signals into higher voltage or current signals to operate said fill and drain control valves;

(h) a second electrical power supply and interface circuit electrically connected to said load cell to convert low voltage signals generated by said load cell into data signals;

(i) computing means for controlling the operation of said fill and drain control valves via said first electrical power supply and interface circuit, and for receiving data signals from said second electrical power supply and interface circuit, said data signals being representative of the weight that is being measured by said load cell;

(j) a set of tubing for transferring liquids, said set of tubing comprising:

(1) a first length of tubing having a first end connected to said at least one fluid exchange bag and a second free end;

(2) a second length of tubing having a first end connected to said at least one fluid drain bag and a second free end;

(3) a third length of tubing having a first end operatively connected to said patient's peritoneal space and a second free end;

(4) fitting means for interconnecting said free ends of said first, second and third lengths of tubing;

(k) said fill control valve being associated with said first length of tubing; and (l) said drain control valve being associated with said second length of tubing.

2. The peritoneal dialysis cycler claimed in claim 1 wherein said stand has means for disassembly into compact parts for portability.

3. The peritoneal dialysis cycler claimed in claim 1 wherein said computing means comprises a laptop microcomputer having at least one input/output port.

4. The peritoneal dialysis cycler claimed in claim 1, wherein substantially zero force is required for said association of said fill control valve with said first length of tubing, and said drain control valve with said second length of tubing.

5. The peritoneal dialysis cycler claimed in claim 1, wherein each of said fill and drain control valves comprises a solenoid valve means for controlling the flow of fluid within a collapsible tube, a body, a plunger contained within a bore of said body, said plunger being axially shiftable between an extended, closed position and a retracted, open position, spring means for biasing said plunger to one of said open and closed positions, electrically-operated coil means for axially shifting said plunger to the other of said open and closed positions, said plunger terminating at one end in a tube-contacting nose portion, a shallow grove in an end surface of the body, said groove extending transversely thereof, said groove intersecting said bore; a member pivotable between a first position wherein it overlies said groove in parallel spaced relationship to said body end surface and a second position remote from said groove, handle means on said member for manually shifting said member between said first and second positions, said second position enabling easy placement of said collapsible tube in said groove, and said first position retaining said collapsible tube within said groove, a portion of said member being chamfered such that said member can be shifted to said first position over said groove and said collapsible tube requiring substantially zero force, and said plunger and nose portion, when in said extended, closed position, collapsing said collapsible tube against said member to preclude fluid flow through said tube.

6. In a solenoid valve means for controlling the flow of fluid within a collapsible tube, a body, a plunger contained within a bore of said body, said plunger being axially shiftable between an extended, closed position and a retracted, open position, spring means for biasing said plunger to one of said open and closed positions, electrically-operated coil means for axially shifting said plunger to the other of said open and closed positions, said plunger terminating at one end in a tube-contacting nose portion, the improvement comprising:

(a) a shallow grove in an end surface of the body, said groove extending transversely thereof, said groove intersecting said bore, which is proximal to said nose portion;

(b) a member pivotable between a first position wherein it overlies said groove in parallel spaced relationship to said body end surface and a second position remote from said groove, handle means on said member for manually shifting said member between said first and second positions, said second position enabling easy placement of said collapsible tube in said groove and said first position retaining said collapsible tube within said groove, a portion of said member being chamfered such that said member can be shifted to said first position over said groove and said collapsible tube requiring substantially zero force, and said plunger and nose portion, when in said extended, closed position, collapsing said collapsible tube against said member to preclude fluid flow through said tube.

7. A solenoid valve as recited in claim 6, wherein said plunger and nose portion are in said extended, closed position when the valve is de-energized.

8. A solenoid valve as recited in claim 6, wherein said plunger and nose portion are in said retracted open position when the valve is de-energized.

9. A method of performing peritoneal dialysis upon a patient, said method comprising the following steps: (a) providing a peritoneal dialysis cycler of the gravity-type which includes a single load cell supporting at least one fluid exchange bag and at least one fluid drain bag, a fill control valve and a drain control valve, computing means for controlling the operation of said fill and drain control valves via electrical interfacing circuitry, a set of tubing for transferring liquids from said at least one fluid exchange bag into the patient via said fill control valve, and a set of tubing for transferring liquids into said at least one fluid drain bag from the patient via said drain control valve;

(b) providing the patient with start-up instructions for a dialysis procedure of one or more cycles, via a video monitor under the control of said computing means, said start-up instructions including options for operating the cycler in manual or automatic mode, options for predetermining amounts of infusate and drain fluids, and options for controlling the timing parameters of each cycle by entering information into said computing means before the commencement of the overall dialysis procedure;

(c) commencing the dialysis procedure which comprises for each cycle thereof the additional steps of:

(1) measuring the gross weight supported by said load cell at the start of each cycle, including said at least one fluid exchange bag and said at least one fluid drain bag, to establish a first reference gross weight for that cycle;

(2) filling the patient's peritoneal space with infusate fluid by opening said fill control valve while keeping said drain control valve in a closed position;

(3) periodically measuring the gross weight supported by said load cell during said filling step and comparing said gross weights to said first reference gross weight and thereby periodically determining the differential weight of infusate fluid which has passed into the patient;

(4) stopping said filling step by closing said fill control valve via said computing means when said differential weight at least equals a predetermined value entered in said computing means;

(5) retaining the infusate fluid within the patient's peritoneal space for a predetermined dwell time interval by maintaining both fill and drain control valves closed;

(6) at the end of said predetermined dwell time, measuring the gross weight supported by said load cell to establish a second reference gross weight for that cycle;

(7) draining the patient's peritoneal space by opening said drain control valve while keeping the fill control valve in a closed position;

(8) periodically measuring the gross weight supported by said load cell during said draining step and comparing said gross weights to said second reference gross weight and thereby periodically determining the differential weight of fluid which has drained from the patient;

(9) stopping said draining step by closing said drain control valve via said computing means when said differential weight of said drain fluid at least equals a predetermined value entered in said computing means;

(10) performing any additional cycles of said dialysis procedure according to steps 1 through 9; and (d) providing the patient with the results of the completed dialysis procedure via said video monitor under the control of said computing means, including in said results information as to how much infusate fluid was placed into the patient's peritoneal space and how much fluid was drained from the patient's peritoneal space during each of said cycles.

10. A method as recited in claim 9, including the step of causing an alarm condition when a flow restriction occurs in either said set of tubing for transferring liquids from said at least one fluid exchange bag into the patient, or said set of tubing for transferring liquids into said at least one fluid drain bag from the patient.

11. A method as recited in claim 10, including the step of causing said computing means to display restart information on said video monitor for the patient's further use of the peritoneal dialysis cycler upon the occurrence of said alarm condition.

12. A method as recited in claim 9, including the step of storing the results of the completed dialysis cycle onto a magnetic disk storage device under the control of said computing means.

13. A method as recited in claim 9, including the step of supplying a first voltage amplitude to each of said fill and drain control valves, for energizing said fill and drain control valves as required, to enable said fill and drain control valves to quickly and affirmatively change state from their de-energized positions to their energized positions, and, after a predetermined time interval, supplying a second voltage amplitude to each of said fill and drain control valves, as required, sufficient for maintaining said fill and drain control valves in their steady-state energized positions, said second voltage amplitude being less than said first voltage amplitude.

* * * * *